United States Patent
Williams et al.

(10) Patent No.: US 9,557,132 B2
(45) Date of Patent: Jan. 31, 2017

(54) FRYER DRAIN CLEANER

(71) Applicant: Otis Products, Inc., Lyons Falls, NY (US)

(72) Inventors: Nicholas Williams, Naples, FL (US); Lawrence Williams, Turin, NY (US)

(73) Assignee: Otis Products, Inc., Lyons Falls, NY (US)

( * ) Notice: Subject to any disclaimer, the term of this patent is extended or adjusted under 35 U.S.C. 154(b) by 0 days.

(21) Appl. No.: 14/149,007

(22) Filed: Jan. 7, 2014

(65) Prior Publication Data
US 2014/0124002 A1 May 8, 2014

Related U.S. Application Data

(63) Continuation-in-part of application No. 13/785,966, filed on Mar. 5, 2013, now Pat. No. 9,115,945.

(60) Provisional application No. 61/724,012, filed on Nov. 8, 2012.

(51) Int. Cl.
  *B08B 9/043* (2006.01)
  *F41A 29/02* (2006.01)
  *B08B 9/04* (2006.01)

(52) U.S. Cl.
  CPC ............ *F41A 29/02* (2013.01); *B08B 9/04* (2013.01); *B08B 9/0436* (2013.01)

(58) Field of Classification Search
  CPC ......... B08B 9/027; B08B 9/043; B08B 9/0436
  USPC ........................................ 15/104.35, 104.16
  See application file for complete search history.

(56) References Cited

U.S. PATENT DOCUMENTS

| | | | | |
|---|---|---|---|---|
| 1,525,933 | A * | 2/1925 | Haigh | 15/104.165 |
| 4,937,907 | A * | 7/1990 | Antal | 15/104.061 |
| 6,546,581 | B1 * | 4/2003 | Swietlik et al. | 15/104.16 |
| 6,775,872 | B1 * | 8/2004 | Appleton et al. | 15/104.16 |
| 6,868,575 | B2 * | 3/2005 | Koregelos | 15/104.04 |
| 8,250,800 | B1 * | 8/2012 | Johnson | 42/95 |
| 8,371,057 | B2 * | 2/2013 | Coffield, III | 42/95 |
| 8,695,264 | B1 * | 4/2014 | Blackburn et al. | 42/95 |
| 8,793,918 | B2 * | 8/2014 | Rogers et al. | 42/95 |
| 2001/0016962 | A1 * | 8/2001 | Moore et al. | 15/104.16 |
| 2006/0162223 | A1 * | 7/2006 | Whipple | 42/95 |
| 2010/0294316 | A1 * | 11/2010 | Antal et al. | 134/22.12 |
| 2011/0174425 | A1 * | 7/2011 | Moreno et al. | 156/91 |
| 2012/0137458 | A1 * | 6/2012 | Knapp | 15/104.061 |

FOREIGN PATENT DOCUMENTS

GB  2465352 A  *  5/2010  ............. B08B 9/055

* cited by examiner

*Primary Examiner* — Michael Jennings
(74) *Attorney, Agent, or Firm* — Harris Beach PLLC

(57) ABSTRACT

A device for removing grease from a tubular drain includes a central member. The device also includes an overmolded structure having a plurality of overmolded wiping discs and a plurality of overmolded support structures. Each wiping disc is supported by an overmolded support on either side of each wiping disc of the plurality of wiping discs. At least one of the plurality of overmolded support structures has at least one hole configured to accept a pin to non-slidingly affix the overmolded structure to the central member. Methods for using the device and for manufacturing the device are also described.

11 Claims, 5 Drawing Sheets

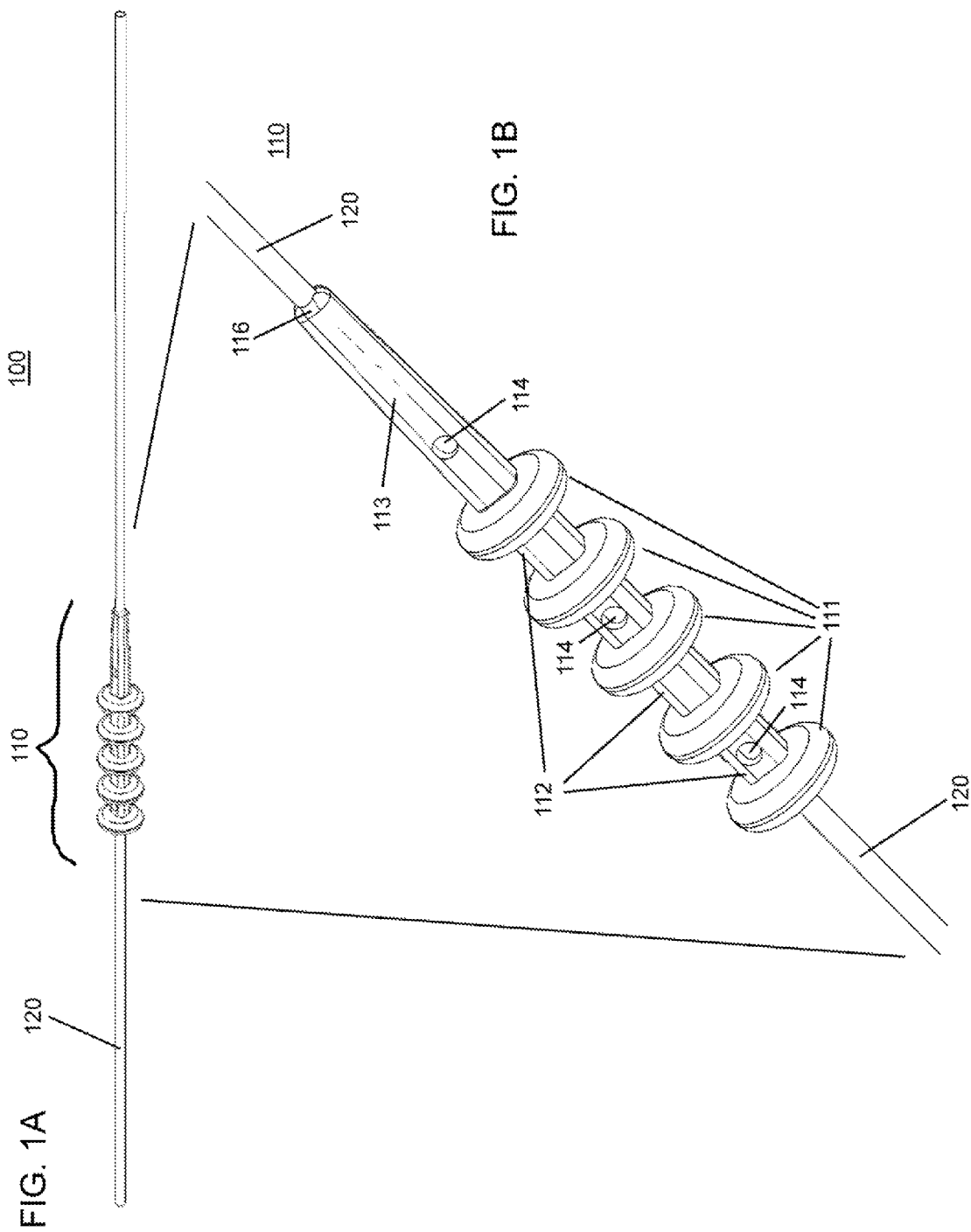

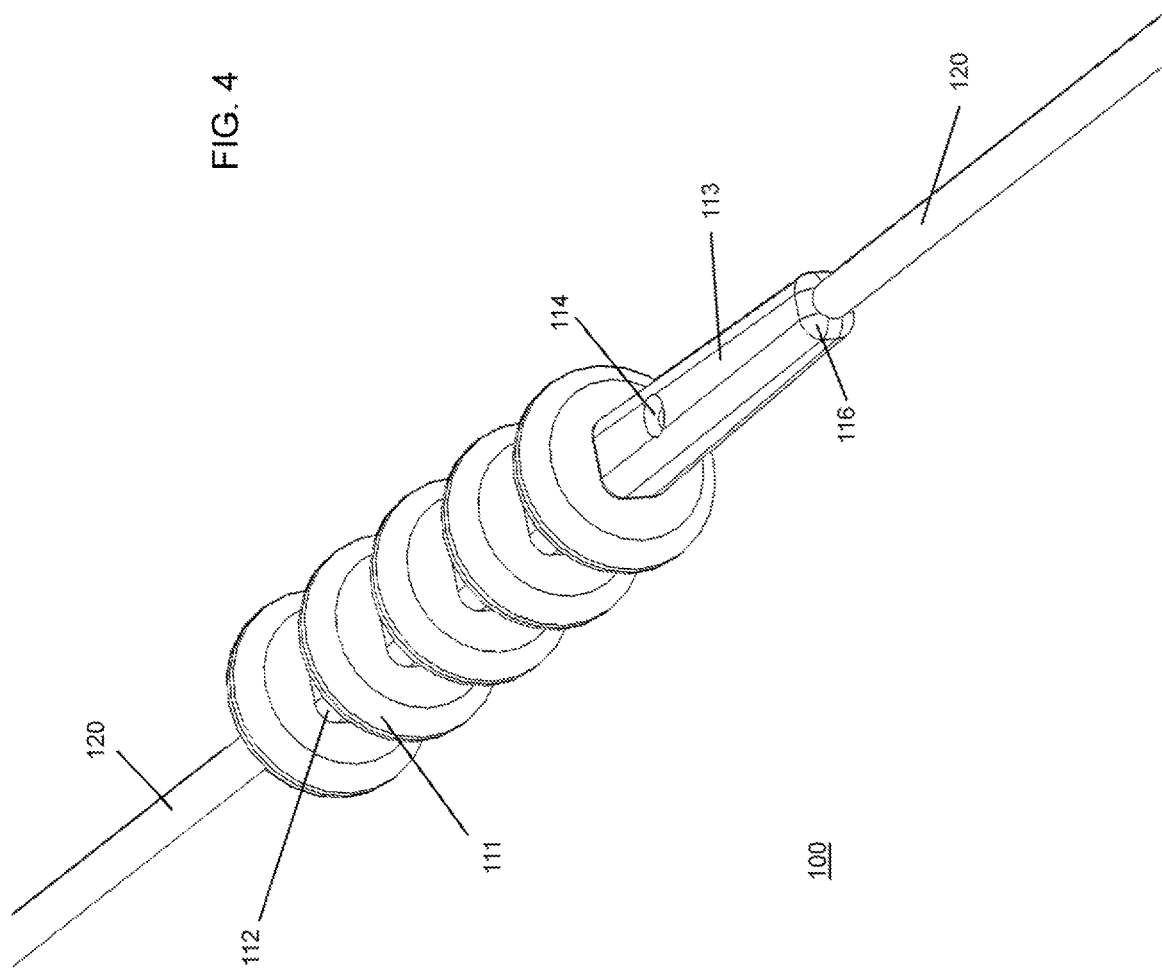

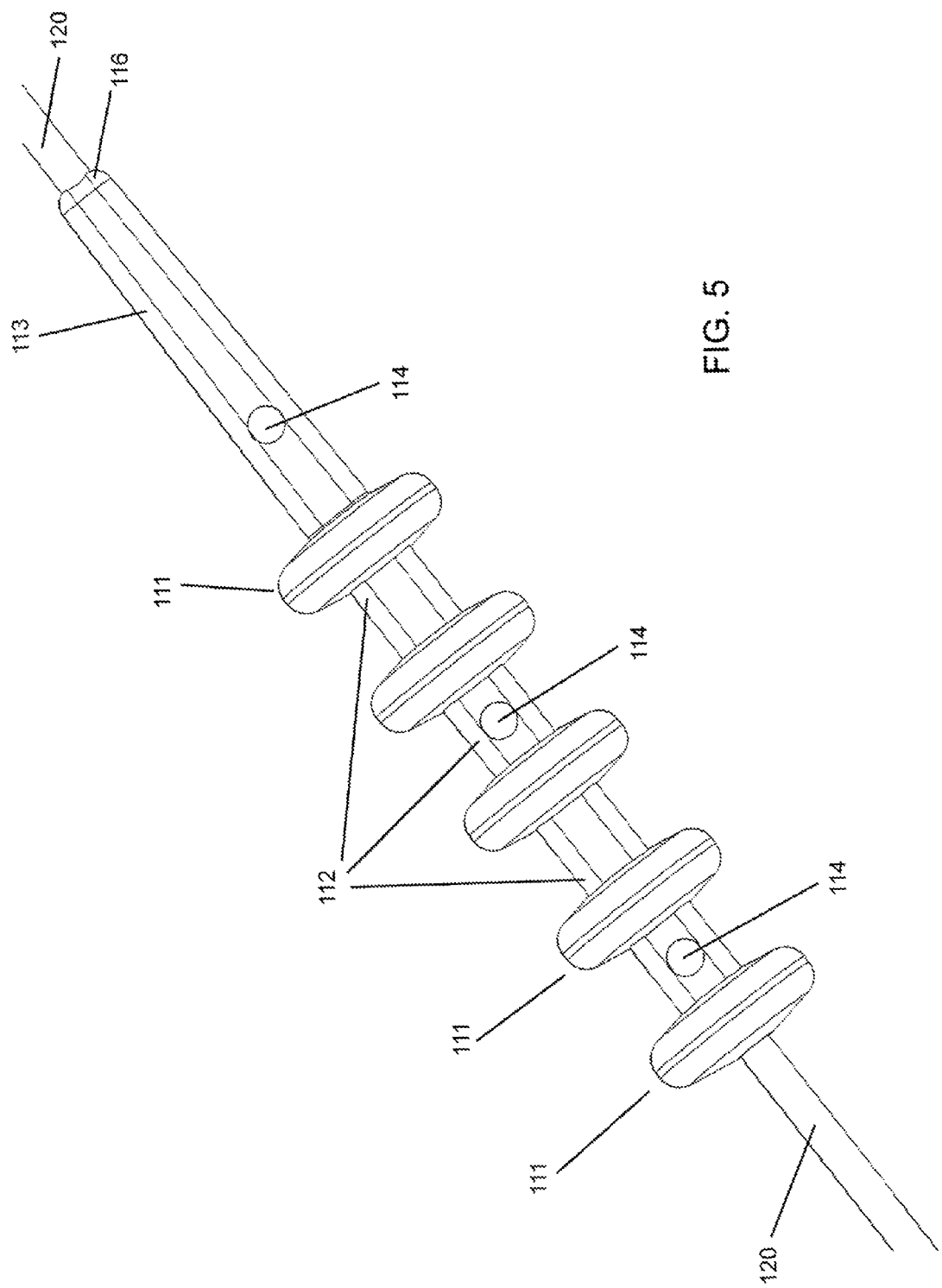

FRYER DRAIN CLEANER

This application is a continuation-in-part of U.S. application Ser. No. 13/785,966, "APPARATUS AND METHOD FOR CLEANING THE BARREL OF A FIREARM" filed Mar. 5, 2013 which claims the benefit under 35 U.S.C. 119(e) to U.S. Application No. 61/724,012, "APPARATUS AND METHOD FOR CLEANING THE BARREL OF A FIREARM" filed Nov. 8, 2012, all of which applications are incorporated herein by reference in their entirety for all purposes.

FIELD OF THE INVENTION

The invention relates to cooking apparatus drain cleaners and particularly to a drain cleaner device to remove grease from a fryer drain.

BACKGROUND OF THE INVENTION

Fryer drain cleaning has been problematic. Existing fryer drain cleaners are generally formed from a stiff wire. The wire is used to punch holes through built up accumulations of grease in drains. While somewhat effective in punching a hole through accumulated grease to promote grease draining, wires such as a single steel wire tend to leave significant undesirable grease build up on the inside wall of the drain.

SUMMARY OF THE INVENTION

According to one aspect, a device for removing grease from a tubular drain includes a central member. The device also includes an overmolded structure having a plurality of overmolded wiping discs and a plurality of overmolded support structures. Each wiping disc is supported by an overmolded support on either side of each wiping disc of the plurality of wiping discs. At least one of the plurality of overmolded support structures has at least one hole configured to accept a pin to non-slidingly affix the overmolded structure to the central member.

In one embodiment, the device for removing grease from the tubular drain further includes at least one elongated or extended overmolded support structure before a first wiping disc or following a last wiping disc of the plurality of wiping discs.

In another embodiment, the at least one extended over molded support section includes a taper from a first wiping disc or from a last wiping disc to a distal end.

In yet another embodiment, the elongated or extended overmolded support structure includes at least one surface configure to accept a product brand selected from the group consisting of model number, company name, product name, and company logo.

In yet another embodiment, the tubular drain includes a fryer drain.

In yet another embodiment, at least one disc of the plurality of overmolded wiping discs includes a diameter of between about 25% to 1% of an inner diameter (ID) of the tubular drain.

In yet another embodiment, the central member includes a member selected from the group consisting of cord, string, rod, and shaft.

In yet another embodiment, the central member includes nylon.

In yet another embodiment, the central member includes polypropylene.

In yet another embodiment, the overmolded structure includes a thermoplastic.

In yet another embodiment, the overmolded structure includes a thermoplastic elastomer (TPE).

In yet another embodiment, the overmolded structure includes a thermoplastic polyolefin (TPO).

In yet another embodiment, the overmolded structure includes a polystyrene-butadiene-styrene (SBS).

In yet another embodiment, the overmolded structure includes a natural or synthetic rubber.

In yet another embodiment, the overmolded structure includes silicone.

According to another aspect, a method for removing grease from a tube includes the steps of: providing a device for removing grease from a tubular drain central member including a central member, and an overmolded structure including a plurality of overmolded wiping discs and a plurality of overmolded support structures, each wiping disc supported by an overmolded support on either side of each wiping disc of the plurality of wiping discs, at least one of the plurality of overmolded support structures having at least one hole configured to accept a pin to non-slidingly affix the overmolded structure to the central member; inserting the device for removing grease into the tube to be cleaned; pushing or pulling the device for removing grease from the tubular drain central member through the drain; accumulating waste grease to be removed from the tube in a space defined between the wiping discs and over the overmolded support structure; removing the device for removing grease from the tube to be cleaned; and removing and disposing of the waste grease from the space defined between the wiping discs and over the overmolded support structure.

According to yet another aspect, a method for manufacturing tubular drain cleaner includes the steps of: providing a central member; overmolding a structure over the central member including a plurality of overmolded wiping discs and a plurality of overmolded support structures, each wiping disc supported by an overmolded support on either side of each wiping disc of the plurality of wiping discs, at least one of the plurality of overmolded support structures having at least one hole configured to accept a pin to non-slidingly affix the overmolded structure to the central member; and anchoring the overmolded structure to the central member during production by use of the pin inserted into the at least one hole.

In one embodiment, the method further includes an optional step of removing the pin after affixing the overmolded structure to the central member.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1A shows a dimetric view one exemplary embodiment of a fryer drain cleaner;

FIG. 1B is an isometric view showing more detail of the over molded section of the fryer drain cleaner of FIG. 1A;

FIG. 4 shows a perspective of the fryer drain cleaner of FIG. 1A;

FIG. 5 shows a side view of the fryer drain cleaner of FIG. 1A; and

DETAILED DESCRIPTION

Figure 3:
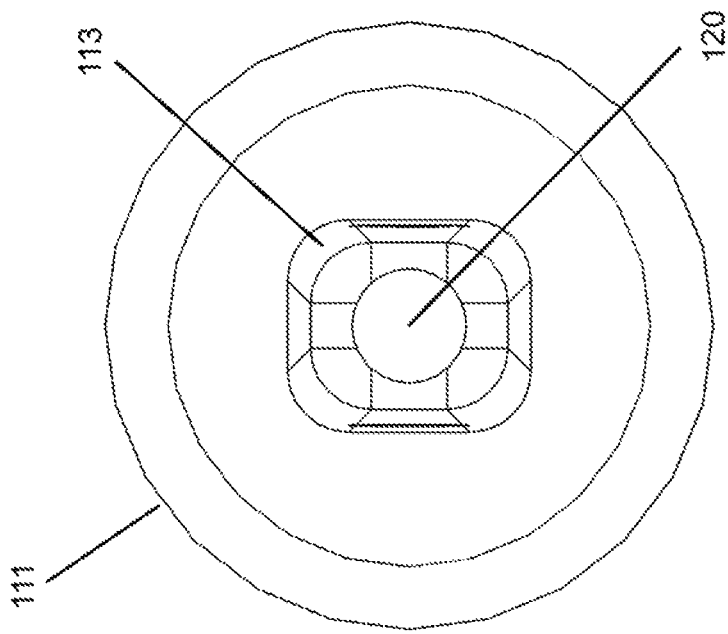
FIG. 3 shows another end view of the fryer drain cleaner of FIG. 1A.

Definitions: Pin, such as a pin to non-slidingly affix an overmolded structure to a central member: As used herein, "pin" includes any suitable pin or pinning means, such as, for example, including pins, screws, set screws (threaded or not threaded), and/or adhesives dropped or otherwise applied in the hole or an adhesive used along with one or more pins, screws, set screws.

There is a need for an improved fryer drain cleaner which can better wipe, clean, and capture waste coagulated grease and other debris in a fryer draining.

FIG. 1A shows a dimetric view one exemplary embodiment of a fryer drain cleaner 100. The exemplary fryer drain cleaner 100 includes an over molded section 110, which can be molded over a central member 120 made from a cord, string, rod, or shaft. In some preferred embodiments, a flexible central member 120 can also be made from polypropylene or nylon. Another advantage of a central member 120 made from polypropylene or nylon is the improved ability to over mold on top of the surface of the central member 120.

FIG. 1B is an isometric view showing more detail of the over molded section 110 of the fryer drain cleaner of FIG. 1A. The over molded section 110 includes wiping discs 111 supported by both central member 120 and over molded supports 112. Over molded supports 112 can be part of a one piece over molded structure. The exact shape of over molded supports 112 is unimportant. One end of the exemplary fryer drain cleaner 100 includes an extended over molded support section 113 (an elongated or extended overmolded support structure having a leading edge 116. In some embodiments, there could be two over molded support sections 113 (not shown in the figures), such as one adjacent to a first wiping disc 111 and the other adjacent to a last wiping disc 111.

In some embodiments of the fryer drain cleaner described herein, extended over molded support section 113 advantageously provides a surface or surfaces for branding the fryer drain cleaner such as by imprinting letters, numbers, and or company logos by any suitable printing, burning, etching, and/or engraving methods. Exemplary markings include model number, company name, product name, and company logo. Also, the shape of extended over molded support section 113 combined with leading edge 116 can help to feed the fryer drain cleaner with its wiping discs 111 through the drain. In some embodiments, the elongated or extended overmolded support structure includes at least one surface configure to accept a product brand such as, for example, a model number, company name, product name, or a company logo.

In some embodiments, wiping discs 111 can be slightly undersized just less than an inner diameter of the intended drain to be cleaned, yet still be made to fit snugly to provide an efficient wiping action. For example, in some embodiments, the diameter of at least one wiping disc can be made between about 25% to about 1% smaller than an inner diameter (ID) of a drain to be cleaned.

The over molded section 110 can be made from any suitable material, such as, for example, plastics, thermoplastics, thermoplastic elastomers (TPE), thermoplastic polyolefin (TPO), polystyrene-butadiene-styrene (SBS), natural or synthetic rubber, and/or silicone. Central member 120 can be any suitable stiff, semi-stiff, or flexible support rod, such as for example, a length of plastic or wire core. Holes 114 can be used to pin over molded section 110 to central member 120. In some embodiments, holes 114 are used during the manufacturing process to hold the wire or string of central member 120 in place while overmolding. Any suitable pin or pinning means can be used, such as, for example, pins, screws, set screws, and/or adhesives dropped in the hole or applied to a pin.

Figure 2:
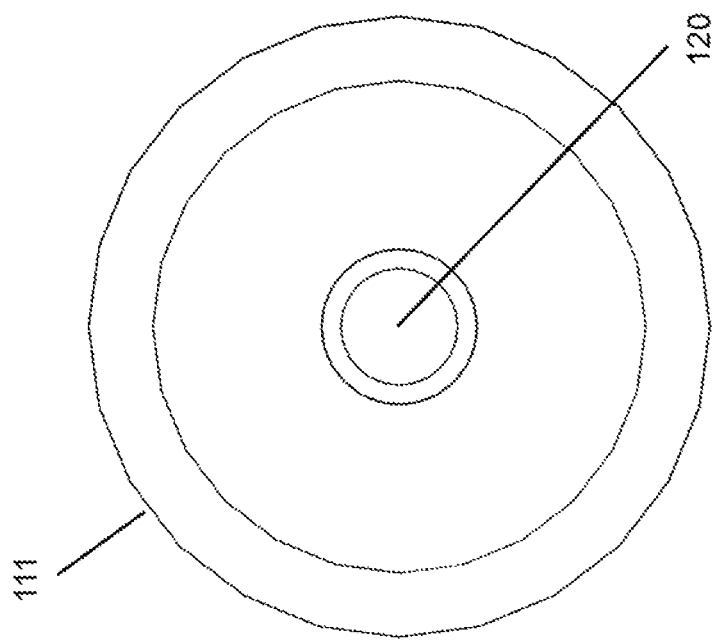
FIG. 2 shows an end view of the fryer drain cleaner of FIG. 1A.
Figure 6:
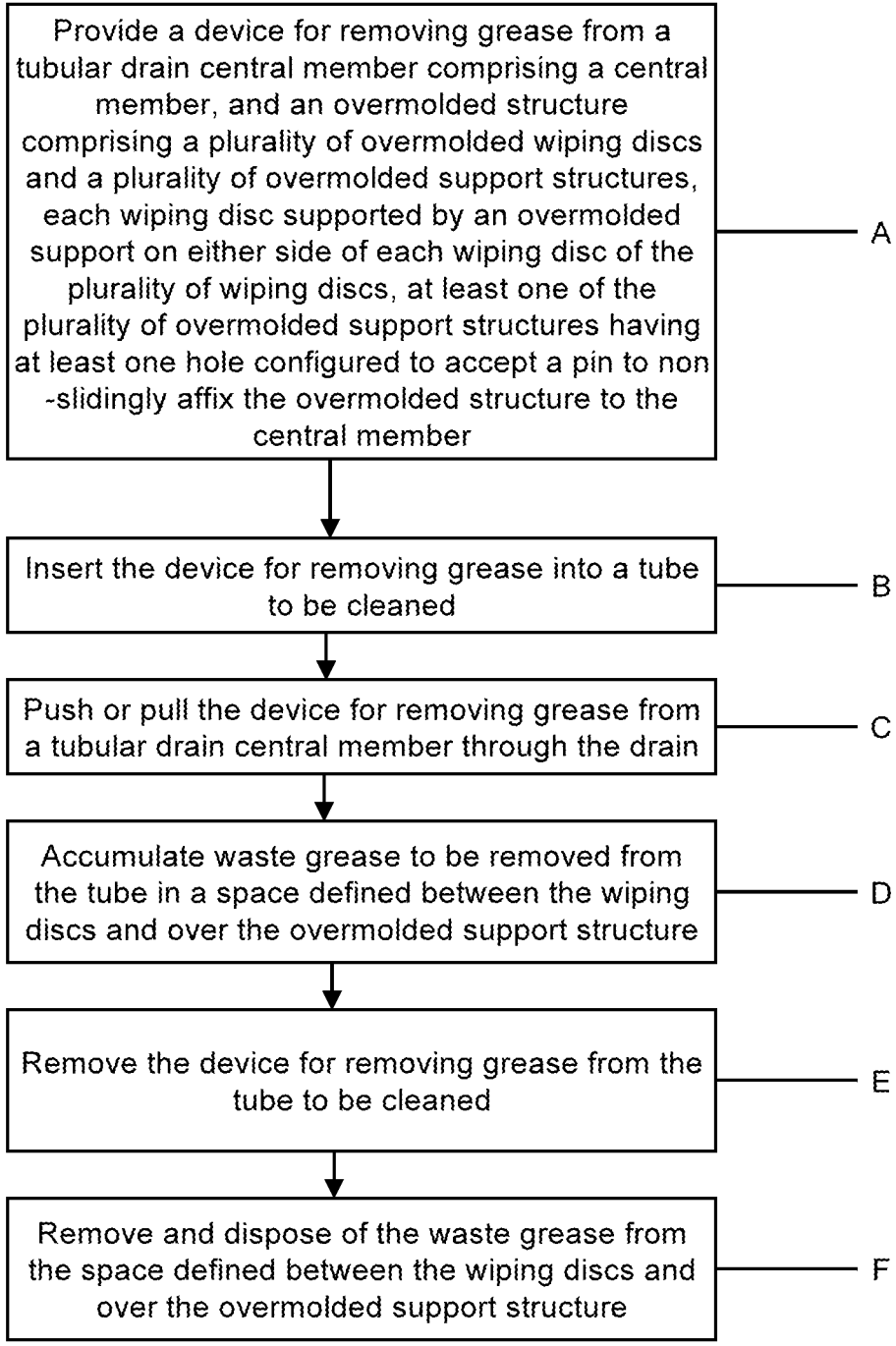
FIG. 6 shows a flow chart of an exemplary method for using the fryer drain cleaner of FIG. 1A.

FIG. 2 shows an end view of the fryer drain cleaner 100 of FIG. 1A. FIG. 3 shows another end view from the side of extended over molded support section 113 of the fryer drain cleaner 100 of FIG. 1A. In this exemplary embodiment, the extended over molded support section 113 can be seen to taper from the last wiping disc 111 to a distal end.

FIG. 4 shows a perspective of the fryer drain cleaner of FIG. 1A better illustrating how the wiping discs 111 can engage the inside diameter of the fryer drain (not shown in FIG. 4) as it is pushed or pulled through the drain. The wiping discs 111, whether or not they directly engage the inner wall of the fryer drain, pull out waste grease and other debris. The waste material can be captured in sections above the over molded supports 112 and between the wiping discs 111 for later removal to a waste receptacle after removal of the fryer drain cleaner 100 from the fryer drain.

FIG. 5 shows a side view of the fryer drain cleaner of FIG. 1A.

Exemplary method of use: A method for removing grease from a tube comprising the steps of: A) provide a device for removing grease from a tubular drain central member comprising a central member, and an overmolded structure comprising a plurality of overmolded wiping discs and a plurality of overmolded support structures, each wiping disc supported by an overmolded support on either side of each wiping disc of the plurality of wiping discs, at least one of the plurality of overmolded support structures having at least one hole configured to accept a pin to non-slidingly affix the overmolded structure to the central member; B) insert the device for removing grease into a tube to be cleaned; C) push and/or pull the device for removing grease from a tubular drain central member through the drain; D) accumulate waste grease to be removed from the tube in a space defined between the wiping discs and over the overmolded support structure; E) remove the device for removing grease from the tube to be cleaned; and F) remove and dispose of the waste grease from the space defined between the wiping discs and over the overmolded support structure.

Exemplary method of production: A method for manufacturing a tubular drain cleaner includes the steps of: A) provide a central member; B) over mold a structure over the central member including a plurality of overmolded wiping discs and a plurality of overmolded support structures, each wiping disc supported by an overmolded support on either side of each wiping disc of the plurality of wiping discs, at least one of the plurality of overmolded support structures having at least one hole configured to accept a pin to non-slidingly affix the overmolded structure to the central member; and C) anchor the overmolded structure to the central member during production by use of the pin inserted into the at least one hole. In some embodiments, there can be an optional step of removing the pin after affixing the overmolded structure to the central member.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A fryer drain cleaner device for removing grease from a fryer tubular drain comprising:
   a central member comprising a polypropylene or a nylon;
   an overmolded section comprising:
      at least five wiping discs integrally molded with said overmolded section;
      at least four overmolded supports integrally molded with said overmolded section and disposed between said at least five wiping discs;
      at least one pin extending through a hole in at least one of said at least four overmolded supports into said central member to pin said overmolded section to said central member; and
      at least one extended over molded support section integrally molded with said overmolded section, said at least one extended over molded support section comprising a taper from a last wiping disc of the five wiping disc towards a distal end of said at least one extended over molded support section, said at least one extended over molded support section having a first outer diameter closest to said last wiping disc of the five wiping disc larger than a second smaller outer diameter at an at least one extended over molded support section end farthest away from said last wiping disc defining said taper, and a leading edge at said distal end of said at least one extended over molded support section.

2. The device of claim 1, wherein said at least one elongated or extended overmolded support structure includes on at least one surface a product brand selected from the group consisting of model number, company name, product name, and company logo.

3. The device of claim 1, wherein said central member comprises a member selected from the group consisting of cord, string, rod, and shaft.

4. The device of claim 1, wherein said central member comprises nylon.

5. The device of claim 1, wherein said central member comprises polypropylene.

6. The device of claim 1, wherein said overmolded structure comprises a thermoplastic.

7. The device of claim 1, wherein said overmolded structure comprises a thermoplastic elastomer (TPE).

8. The device of claim 1, wherein said overmolded structure comprises a thermoplastic polyolefin (TPO).

9. The device of claim 1, wherein said overmolded structure comprises a polystyrene-butadiene-styrene (SBS).

10. The device of claim 1, wherein said overmolded structure comprises a natural or synthetic rubber.

11. The device of claim 1, wherein said overmolded structure comprises silicone.

* * * * *